(12) United States Patent
    Chand

(10) Patent No.: US 8,720,794 B2
(45) Date of Patent: May 13, 2014

(54) GAS PERMEATION DEVICES

(75) Inventor: Ramesh Chand, Chino Hills, CA (US)

(73) Assignee: Real Sensors, Inc., Hayward, CA (US)

( * ) Notice: Subject to any disclaimer, the term of this patent is extended or adjusted under 35 U.S.C. 154(b) by 413 days.

(21) Appl. No.: 13/276,235

(22) Filed: Oct. 18, 2011

(65) Prior Publication Data

US 2012/0091220 A1    Apr. 19, 2012

Related U.S. Application Data

(60) Provisional application No. 61/394,245, filed on Oct. 18, 2010.

(51) Int. Cl.
    *A24F 25/00*    (2006.01)
    *A61L 9/04*     (2006.01)

(52) U.S. Cl.
    USPC ............... 239/34; 239/57; 239/548; 239/575; 239/589; 222/399

(58) Field of Classification Search
    USPC ............ 239/34, 337, 575, 57, 548, 552, 589; 169/11, 12, 30, 35, 84; 222/399
    See application file for complete search history.

(56) References Cited

U.S. PATENT DOCUMENTS

| | | | |
|---|---|---|---|
| 3,412,935 A | | 11/1968 | O'Keeffe |
| 3,763,025 A | | 10/1973 | Chand |
| 3,788,545 A | * | 1/1974 | Budd et al. ...................... 239/34 |
| 3,856,204 A | | 12/1974 | Chand |
| 4,399,942 A | | 8/1983 | Chand |
| 5,310,838 A | | 5/1994 | Hung et al. |
| 5,326,839 A | | 7/1994 | Resnick |
| 5,338,608 A | | 8/1994 | Resnick |
| 5,353,368 A | | 10/1994 | Hung et al. |
| 5,354,910 A | | 10/1994 | Hung et al. |
| 5,408,020 A | | 4/1995 | Hung et al. |
| 7,455,120 B2 | * | 11/2008 | Richardson et al. ............ 169/12 |
| 7,614,568 B2 | * | 11/2009 | Joshi et al. ...................... 239/34 |

* cited by examiner

*Primary Examiner* — Steven J Ganey
(74) *Attorney, Agent, or Firm* — Steven A. Nielsen; Allman & Nielsen, P.C.

(57) ABSTRACT

A system used for permeating or emitting a gas or a chemical at a constant, predictable and controllable rate uses an amorphous fluoropolymer material as a gateway. The system may comprise a tube assembly which holds a gas or liquid. The gas or liquid permeates though the fluoropolymer material to be released in precise quantity, resulting in known concentrations of the gas, when mixed with a flowing or carrier gas such as air or nitrogen.

6 Claims, 10 Drawing Sheets

GAS PERMEATION DEVICES

CROSS-REFERENCE TO RELATED APPLICATIONS

This is a utility application based upon U.S. patent application Ser. No. 61/394,245 filed on Oct. 18, 2010. This related application is incorporated herein by reference and made a part of this application. If any conflict arises between the disclosure of the invention in this utility application and that in the related provisional application, the disclosure in this utility application shall govern. Moreover, the inventor(s) incorporate herein by reference any and all patents, patent applications, and other documents hard copy or electronic, cited or referred to in this application.

BACKGROUND OF THE INVENTION (1) Field of the Invention

The invention generally relates to gas permeating or gas emitting systems. More particularly, the invention relates to a gas permeating system using an amorphous fluorpolymer material.

(2) Description of the Related Art

Other permeation devices or tube devices are known in the related art and are widely used to deliver or generate known gas mixtures of various chemicals. Devices in the related art are used for the testing and calibration of air pollution instruments, chemical and petrochemical process analyzers and safety equipment.

An early device was disclosed by Andrew E. O'Keefe in his U.S. Pat. No. 3,412,935 (the '935 patent). In the '935 patent O'Keefe describes the use of material such as sulfur dioxide kept inside a tube made with polytetrafluoroethylene (PTFE), in the form of liquefied gas under its own pressure. The sulfur dioxide will permeate in the form of gas through the solid wall of the PTFE tubing, and the rate remained fairly constant, as long as the tube was kept at a contestant temperature. The permeation rate was however, low generating concentrations in low ppm (parts per million) range; and the permeation rate was substantially dependent on the temperature of the device, in the range of 10 to 15% increase for every one (1) degree Celsius increase in temperature. Similar results have been obtained with other materials such as fluorinated ethylene-propylene (FEP), perfluoroalkoxy fluorocarbon (PFA) and others.

Subsequently, Chand in U.S. Pat. Nos. 3,856,204 and 4,399,942 described the use of silicone material to obtain higher permeation rates and low temperature dependency. However, the use of silicone has been limited to mostly non-corrosive materials and was found unsuitable for gases like nitrogen dioxide and sulfur dioxide.

Paul R. Resnick, Min-Hong Hung and others have developed various types of amorphous fluoropholymer material, more formally known as fluorinated (ethylenic-cyclo oxyaliphatic substituted ethylenic) copolymer, with certain variations commonly known as Teflon AF as a trade name sometimes associated with I.E. Du Pont de Nemours and Company.

In U.S. Pat. No. 5,310,838 issued on May 10, 1994 Hung and Resnick disclosed a Fluoropolymer comprising repeat units of perfluoro-2,2-dimethly-1,3-dioxole with a repeat unit of another fluoromonomer such as tetrafluoroethylene.

In U.S. Pat. No. 5,324,889 issued on Jun. 28, 1994 Resnick disclosed various amorphous perfluoropolymers directed toward the use of cladding materials for optical fibers, encapsulating materials for electronic components, laminates other uses were impervious surfaces were needed.

As the use of silicone in permeation devices has limitations regarding the use of corrosive material there is room in the art for new means and methods of creating gas permeation devices. While the known prior art uses various types of amorphous fluoropholymer materials for impervious surfaces there is room in the art for unobvious or more artful uses for amorphous fluoropholymer materials.

BRIEF SUMMARY OF THE INVENTION

The embodiments of the present inventions overcomes shortfalls in the related art by presenting an unobvious and unique combination, configuration and use of an amorphous fluoropolymer material [chemical name: fluorinated (ethylenic-cyclo oxyaliphatic substituted ethylenic) copolymer], as the material through which gas permeates within disclosed embodiments of gas permeation devices.

One embodiment of amorphous fluoropolymer material is made by E.I. DuPont Company and is marketed under their trade name Teflon AF. The disclosed gas permeation devices made with Teflon AF produced unexpected results with superior permeation rates substantially higher as compared to other known materials. Moreover, the disclosed devices have shown much less temperature dependency and are useful for the controlled release of materials which were found too corrosive for the silicone material of the related art.

The unexpected results of the disclosed devices are supported in the less impressive results reported in the related art. For example, O'Keeffe, in the '935 patent describes the increase in permeation rate of his device made with FEP material to increase almost 100% when the temperature is increased approximately 9 degrees Celsius. Additionally, the usefulness of the O'Keeffe device is limited to the generation of permeation rated less than 1,000 nanograms/minute. While these issues were addressed by Chand in his prior patents, the effective use of the prior art devices was limited to non-corrosive and non-reactive gases to the silicone material. The devices of the prior art were found to be unstable for substances such as sulfur dioxide and nitrogen dioxide.

The novelty and unobvious nature of the disclosed embodiment is supported by unexpectedly good test results. For example, the results obtained with sulfur dioxide showed astounding improvements as compared to the known related art. Permeation rates from less than 200 to over 10,000 nanograms per minute were achieved using Teflon AF. Additionally, the temperature dependency was found to be cut in less than half, as compared to the prior art devices using FEP and PTFE.

Additionally, the embodiments of the present inventions overcome shortfalls in the related art by the artful use and unobvious configuration of membranes made with amorphous fluoropolymer material. For example, in one embodiment, an amorphous fluoropolymer membrane is manufactured with a plurality of protrusions, with the protrusions inserted into voids of a top cap. Membrane protrusions within the top cap voids present a significant and unobvious departure from the related art.

These and other objects and advantages will be made apparent when considering the following detailed specification when taken in conjunction with the drawings.

REFERENCE NUMERALS IN THE DRAWINGS

Figure 1:
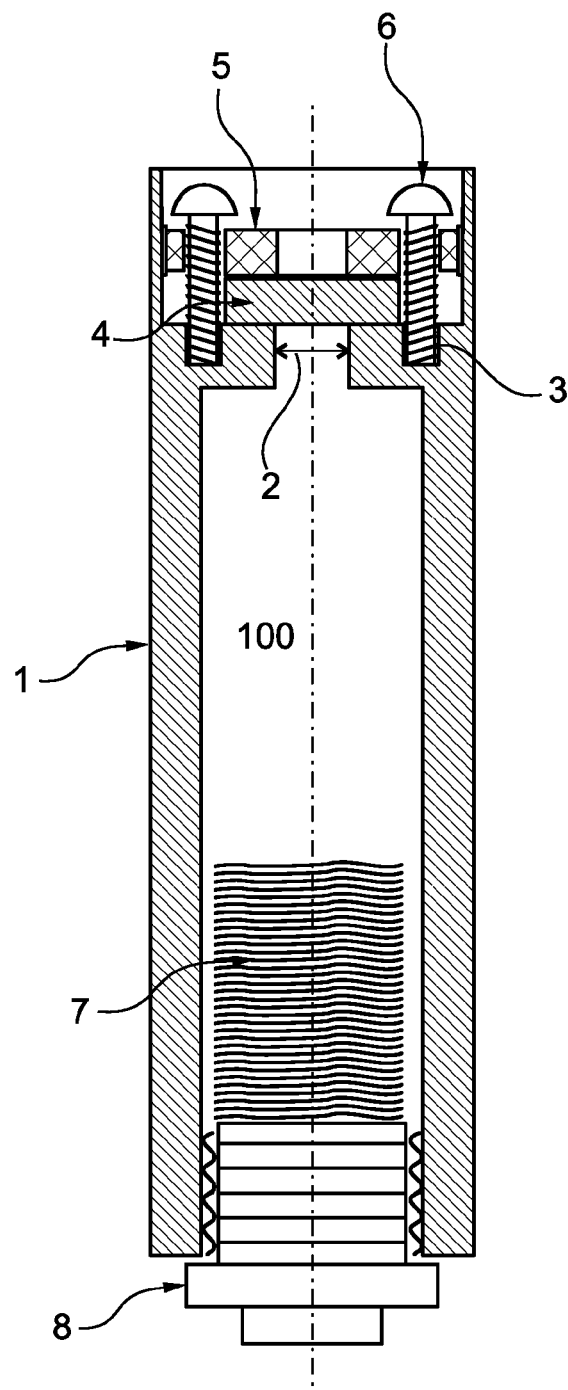
FIG. 1 is a sectional view of a first embodiment of a permeation device made in accordance with the principles of embodiments of the disclosed inventions.

100 a first embodiment of the invention in general
1 a hollow tube
2 opening of tube, on top side
3 tapped voids within the body
4 a film of amorphous fluoropolymer, such as Teflon AF
5 gasket
6 screws
7 gas contained within the device
8 pipe plug
200 a second embodiment of the invention in general
201 tube of second embodiment
202 a constricted opening within the tube 201, the constricted opening 202 being a passage way between the main chamber 210 of the tube and the void 218 for the membrane
203 tapped or drilled voids within a top cap, also called screw voids
204 a permeable membrane, a film or membrane of amorphous fluoropolymer, such as Teflon AF
205 a gasket for the second embodiment
206 screws of the second embodiment
207 gas contained within the device
208 pipe plug of the second embodiment
210 main chamber of tube 201
211 neck area of device of the second embodiment
215 shole voids or sholes used for gas movement
216 center shole void
217 shole protrusions or protrusions at perimeter of the membrane
218 a void or a membrane void sometimes used to hold a membrane 204
220 center shole protrusion or center protrusion of the membrane, may fit into center shole void 216
222 pipe plug embodiment
230 top cap
231 bottom side of top cap
232 top side of top cap 220
233 washer
235 flat outer surface of neck area
301 pattern for voids within neck 211 of a device 200
303 voids within the neck area 211

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

Referring to FIG. 1, one embodiment 100 of the invention in general is shown. A hollow tube 1 comprises a top permeation end and a bottom gas filling end. The tube may be constructed with any material that is compatible with gas or other expected contents of the tube. Contemplated materials for tube 1 construction include aluminum, stainless steel, or plastic material with very low permeation or vapor transmission rates. A void 2 found at the top end of the tube has a diameter and size that may be adjusted or controlled to obtain desired permeation rates.

A film of amorphous fluoropolymer material 4 which may include Teflon AF material is shown completely covering top end void 2. The thickness of the amorphous fluoropolymer may be altered or used to control the rate of permeation for a given opening or void. The thickness of the amorphous fluoropolymer material may be any dimension, but is contemplated to be in the range of 1 millimeter to 10 millimeters or thicker. In one embodiment, Teflon AF material may be further covered with a gasket 5, with a suitable opening in the center for gas to flow.

The gasket 5 may be made from any material including rubber, Viton and/or stainless steel. The Teflon AF and gasket assembly may be firmly anchored to a flat body of the device, using screws 6 set in taped holes in the body 3. Generally, four to six screws are found to be sufficient to secure the entire assembly and to keep the entire assembly intact against the pressure exerted by the gas 7 found within the device.

In testing, the device 100 was further filled with gas by cooling the gas to liquefy and to fill the inside of the device. Precautions were taken to ensure that the liquefied gas allowed for expansion inside the device. Most of the chemical sued had vapor pressures less than 300 psig (pounds per square inch). The assembly may be completed by closing the bottom opening with a suitable pipe plug 8.

The novelty and unobvious nature of the disclosed embodiment is supported by unexpectedly good test results. For example, the results obtained with sulfur dioxide showed astounding improvements as compared to the known related art. Permeation rates from less than 200 to over 10,000 nanograms per minute were achieved using Teflon AF. Additionally, the temperature dependency was found to be cut in less than half, as compared to the prior art devices using FEP and PTFE.

The shape of the disclosed membrane, such as Teflon AF, is not limited to a flat membrane and may take the form of a hollow tube or any other suitable configuration. Teflon AF, a material of E.I. Du Pont de Nemours and Company, is a family of amorphous fluoropolymers. Teflon AF and related polymers are described in U.S. Pat. Nos. 4,399,264; 4,485,250; 4,754,009; 4,935,477; 5,276,121; 5,326,839; 5,353,368; 5,324,889; 5,338,608; 5,310,838; 5,354,910; and 5,408,020, all of which are incorporated herein by reference.

Figure 2:
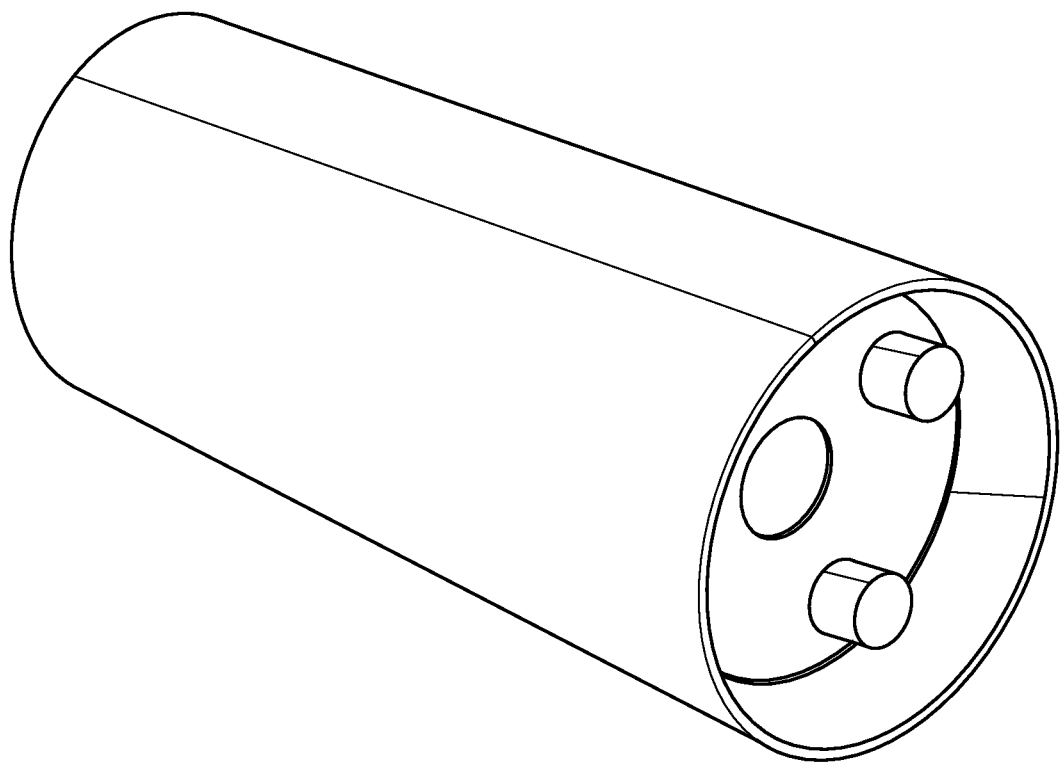
FIG. 2 is a perspective view of first embodiment of a permeation device made in accordance with the principles of embodiments of the disclosed inventions.

FIG. 2 shows a first embodiment 100 consistent with FIG. 1.

Figures 3, 4:
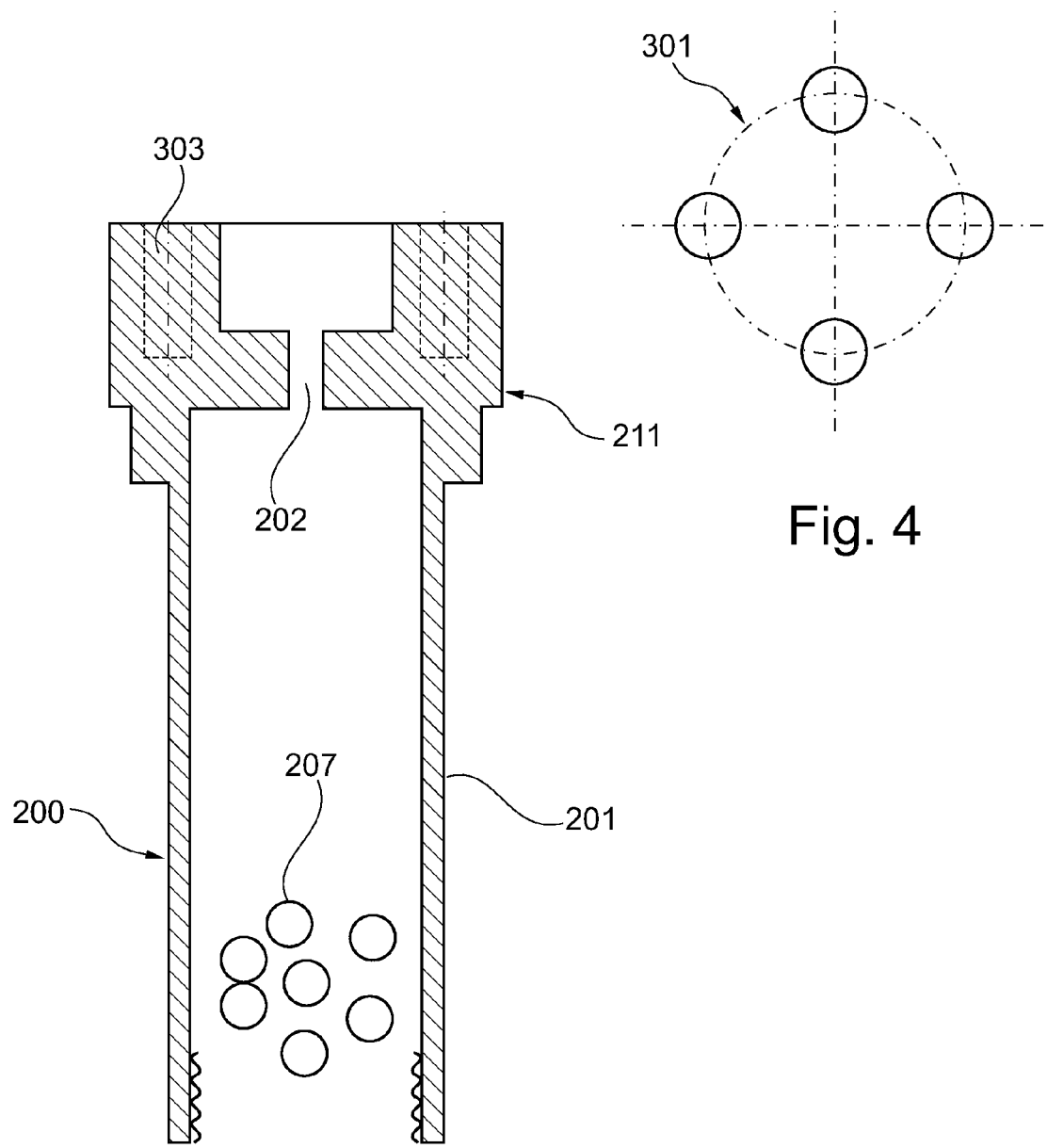
FIG. 3 is a sectional view of a second embodiment of a permeation device made in accordance with the principles of embodiments of the disclosed inventions.
FIG. 4 is a top plan view of void patterns found within a neck area of a permeation device.

FIG. 3 is a sectional view of a second embodiment 200 having a tube 201 containing gas 207 or liquid. The gas 207 or liquid may travel through opening 202 within the tube. The gas opening 202 may be a void defined by a neck area 211 found upon a top portion of the tube 201. The neck area may also define voids 303 used to accept screws.

FIG. 4 presents a top plan view of a pattern 301 sometimes used to set voids 303 into the neck area 211 of a device 200.

Figure 5:
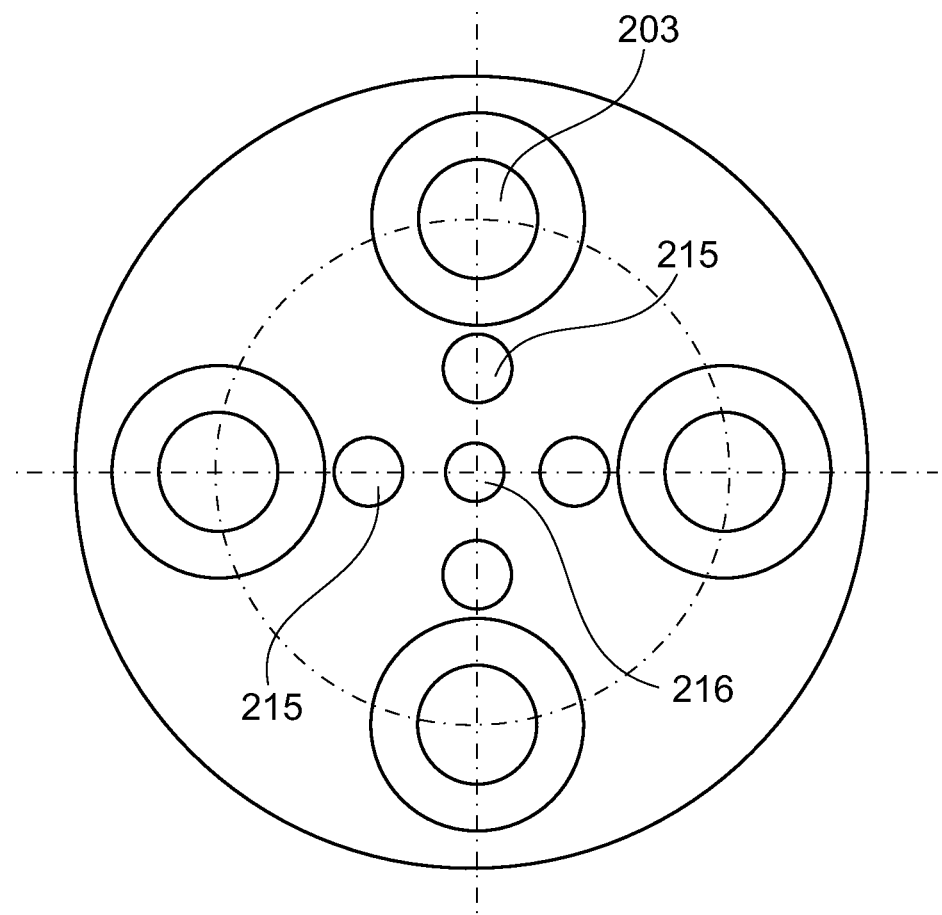
FIG. 5 is a top plan view of a top cap

FIG. 5 shows a top side 232 of a top cap 220, the top cap 220 defining a plurality of tapped or drilled voids 203 used for accepting screws and defining a plurality of shole voids 215 or sholes. The shole voids 215 or sholes are sometimes used to accept protrusions of a membrane. The top cap 220 includes a center shole void 216.

Figure 6:
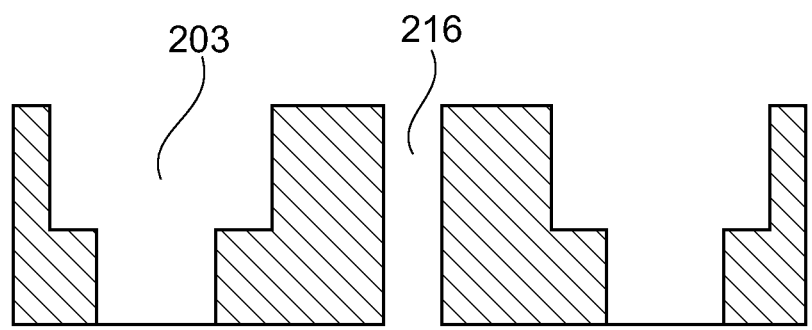
FIG. 6 is a side sectional view of a top cap

FIG. 6 is a sectional view of a top cap, showing voids 203 for screws and a center void or center shole 216 sometimes used to accept a center protrusion from a membrane.

Figure 7:
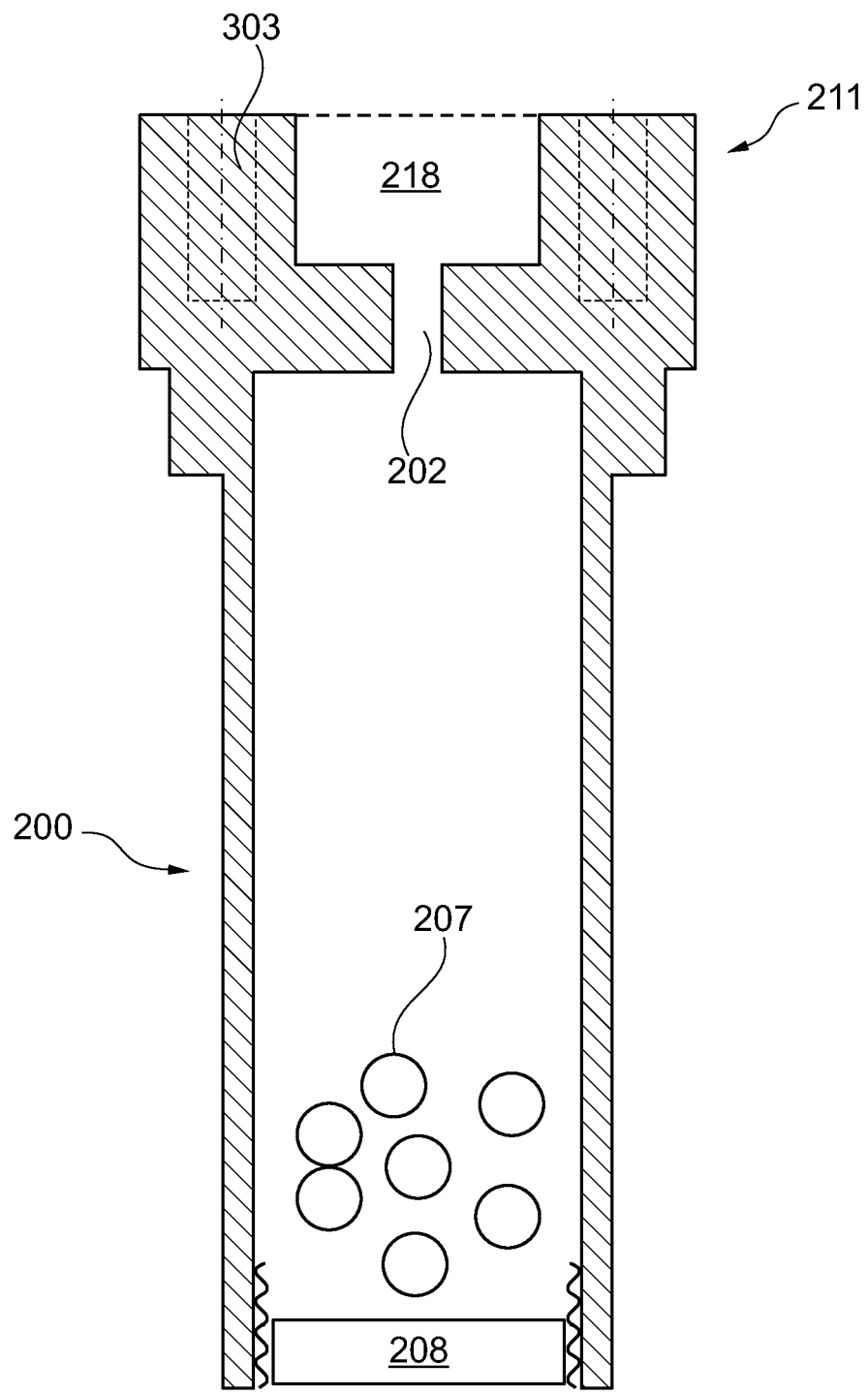
FIG. 7 is a side sectional view of a second embodiment

FIG. 7 is a sectional view of one embodiment and shows a pipe plug 208 embodiment found at the lower of the tube. Above the opening 202 of the neck area 211 is a void 218 for a membrane.

Figure 8:
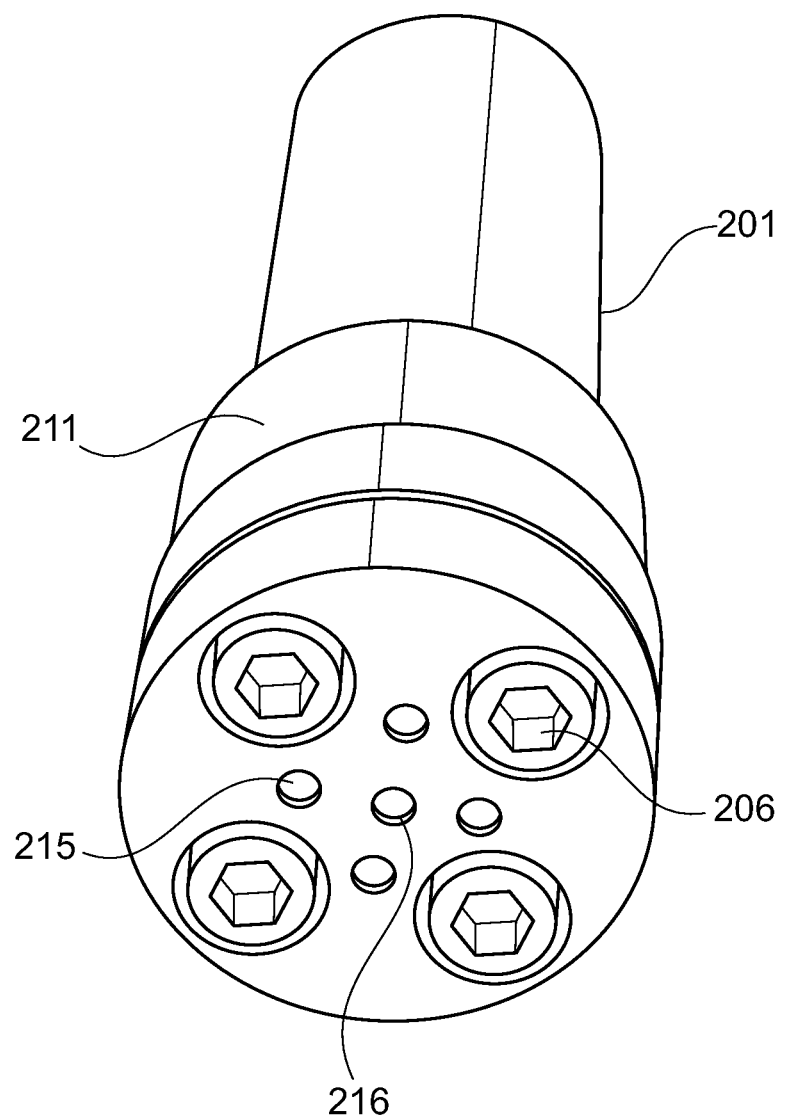
FIG. 8 a perspective view of a second embodiment

FIG. 8 shows a perspective view of one embodiment having screws 206 securing a top cap to a neck 211. The top cap comprises shole voids 215 surrounding a center shole void 216. A tube section 201 is shown in the back ground.

Figure 9:
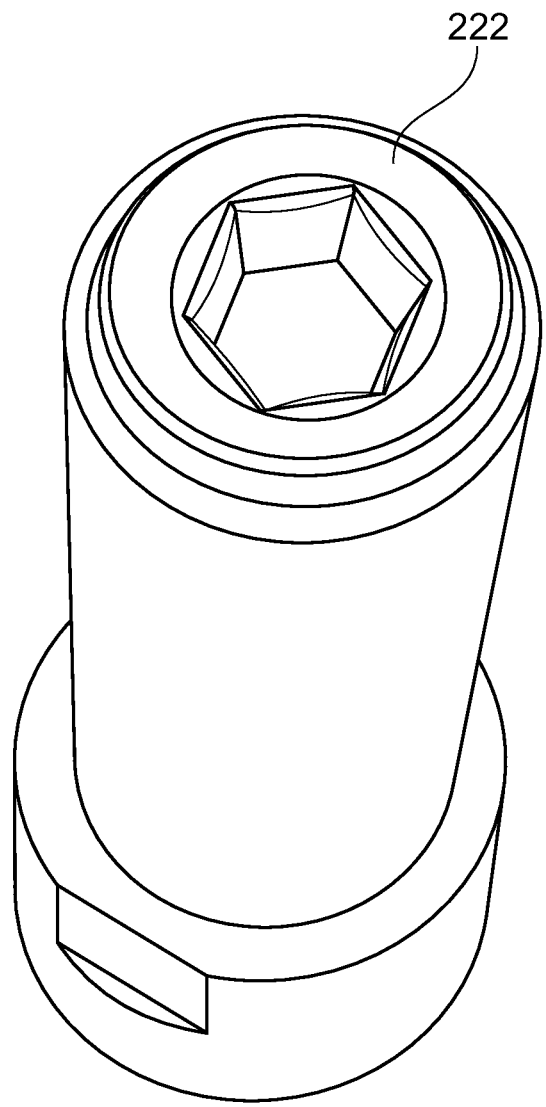
FIG. 9 a perspective view of an end plug embodiment

FIG. 9 shows a pipe plug 222 embodiment.

Figure 10:
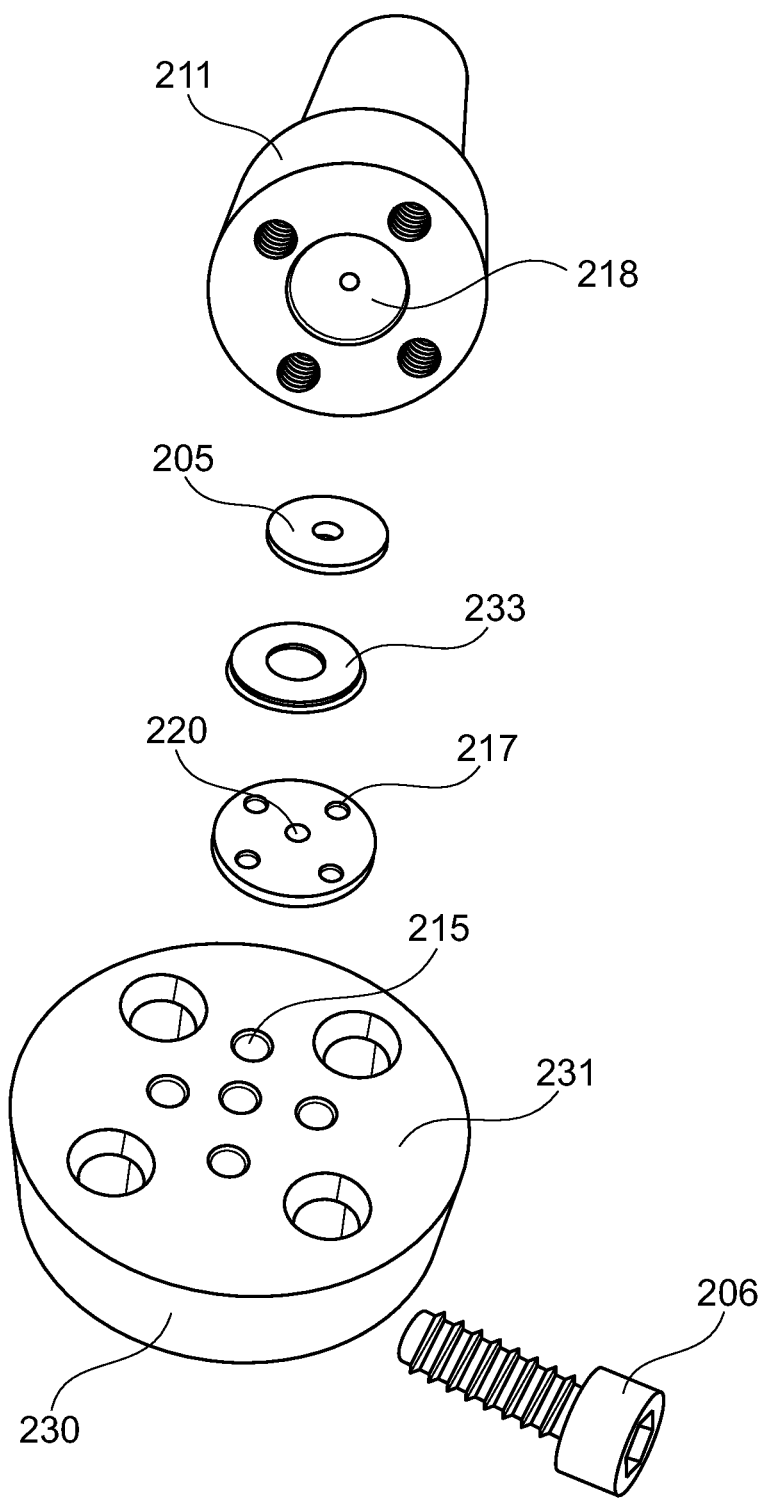
FIG. 10 is an exploded view of a second embodiment

FIG. 10 shows an exploded view of various components of an embodiment. Starting in the foreground, a screw 206 is adjacent to a top cap 230, the top cap having a top side 232 revealing various voids, including a shole void 215. A membrane 204 or film used to control the permeation of gas or fluid may comprise a plurality of shole protrusions 217 or protrusions, sometimes inserted into shole voids 215 of a top cap 230. The film or membrane 204 may also have a center shole protrusion 220. A washer 233 may be placed behind the membrane 204. A gasket 205 may be placed behind a washer 233. The washer, gasket and membrane may be fitted into a void 218 for the membrane, the void 218 defined by a neck section or neck area 211.

Figure 11:
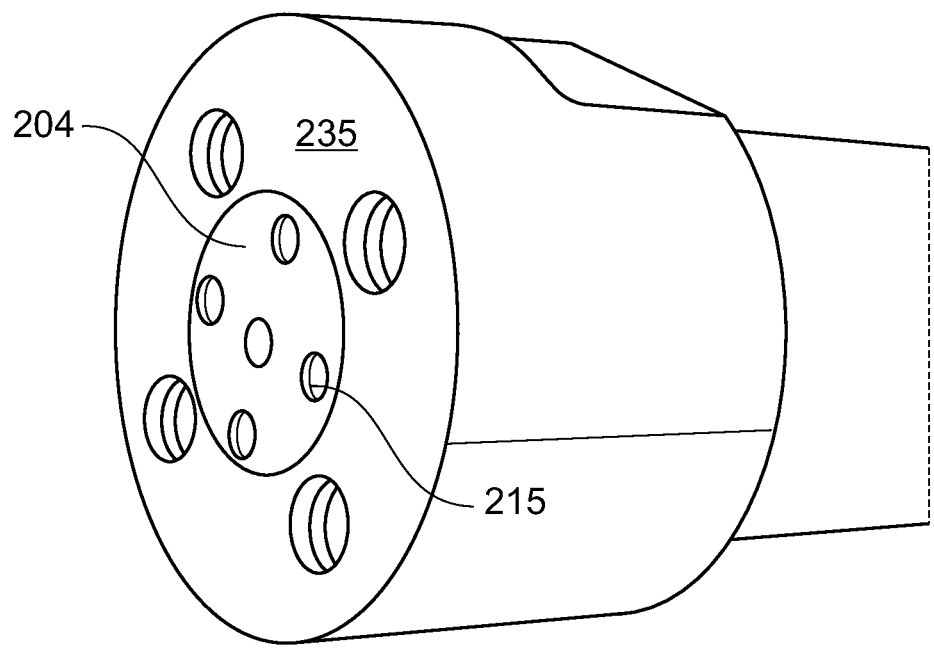
FIG. 11 is a perspective view of a neck section

FIG. 11 presents a side perspective view of a flat outer surface 235 of a neck and a membrane contained within a void of the neck, with the membrane 204 having a plurality of protrusions 217.

Figure 12:
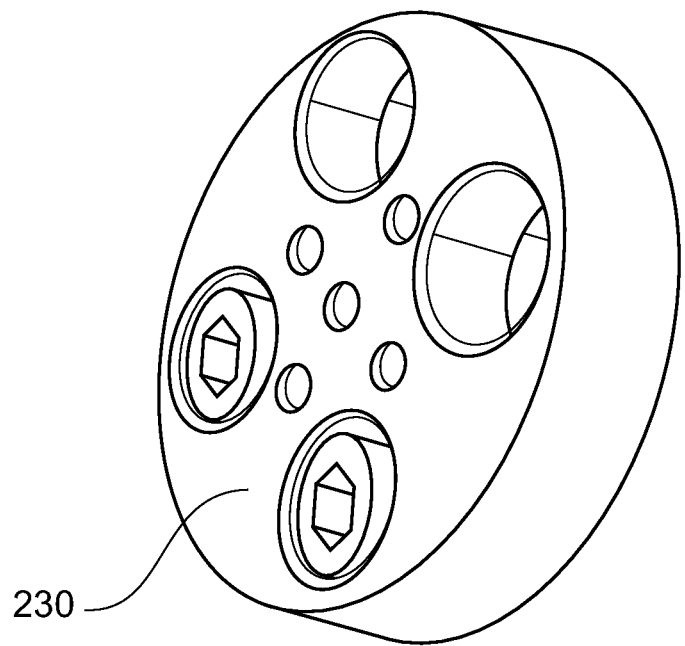
FIG. 12 is a perspective view of a top cap

FIG. 12 presents a top perspective view of a top cap 230 with two screws inserted and two screw voids empty. The top cap of FIG. 12 is shown in approximate alignment for attachment to the flat surface 235 of the neck area of the tube.

Figure 13:
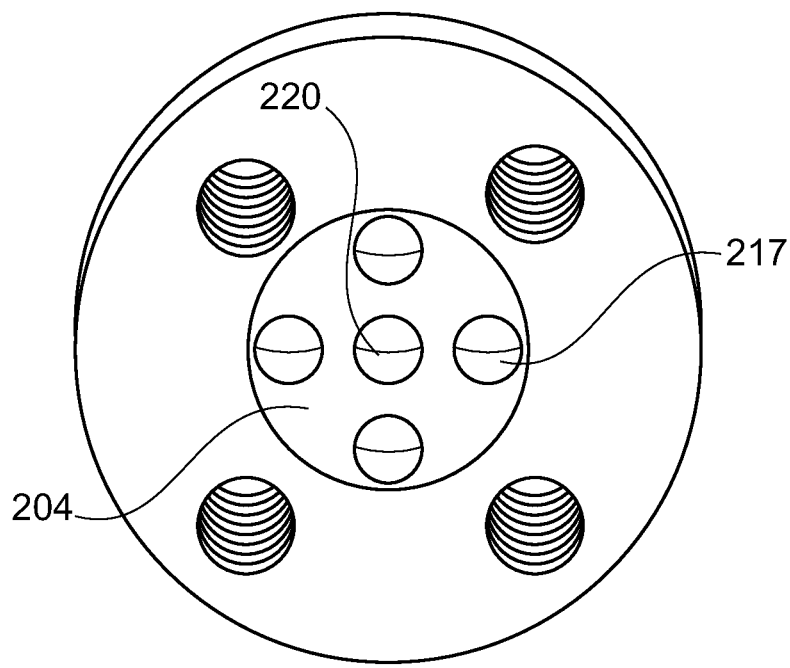
FIG. 13 a perspective view of a membrane and neck

FIG. 13 shows a 204 membrane having a plurality of protrusions 217 and a center protrusion or center shole protrusion 220.

Figure 14:
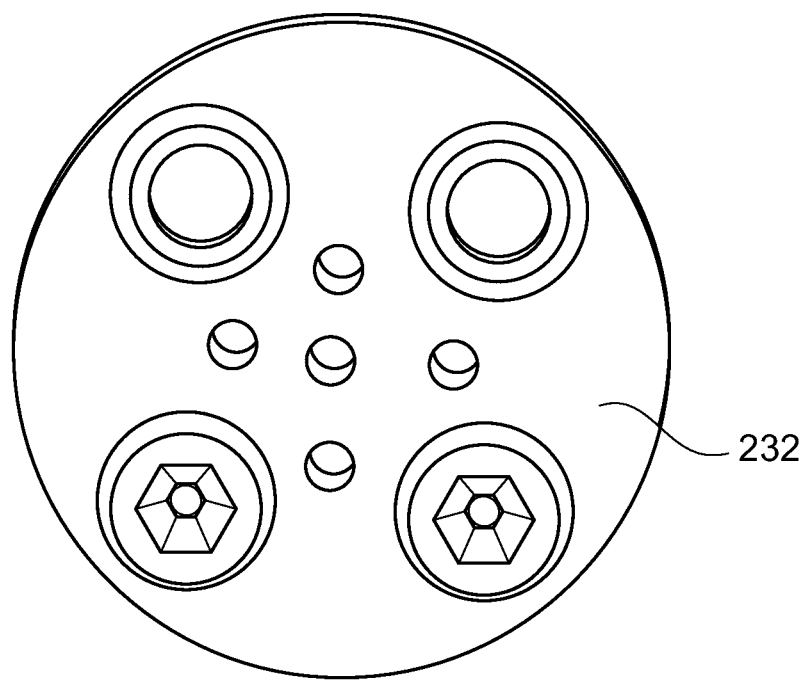
FIG. 14 is a perspective view of a top side of a top cap

FIG. 14 shows a top side 232 of a top cap.

Items.

Disclosed embodiments include the following items.

Item 1. A gas emitting system 200, the system comprising:

a) a tube 201 having a main chamber 210 and the tube 201 having a bottom end attached to a pipe plug 208 and the tube having a top end attached to a neck area 211;

b) the neck area 311 defining a constricted opening 202, with the constricted opening connected to the main chamber 210 and the constricted opening connected to a membrane void 218; the neck area 218 having a flat outer surface 235 and the neck area defining a plurality of voids 303 perpendicular to the flat outer surface 235 of the neck area;

c) a top cap 230 having a bottom side 231 and top side 232, the top cap defining a plurality of screw voids 203;

d) the top cap defining a plurality of shole voids 215, the shole voids surrounding a center shole void 216, the center shole void defined by the top cap; and e) a permeable membrane 204 placed within the membrane void.

Item 2. The system of item 1 wherein a washer 233 is in contact with the permeable membrane and a gasket 205 is in contact with the washer.

Item 3. The system of item 1 wherein the permeable membrane comprises a plurality of protrusions 217 surrounding a center 220 protrusion.

Item 4. The system of item 3 with the plurality of protrusions 217 entering the shole voids 215 of the top cap 230 and with the center protrusion 220 entering the center shole 216 void.

Item 5. The system of item 4 wherein the permeable membrane comprises amorphous fluoropolymer.

Item 6. The system of item 4 wherein the permeable membrane is comprised of fluorinated (ethylenic-cyclo oxyaliphatic substituted ethylenic) copolymer.

Item 7. The system of item 4 wherein the permeable membrane comprises Teflon AF.

Item 8. The system of item 4 wherein a liquid is placed within the main chamber 210 and the liquid passes through the membrane.

Item 9. The system of item 4 wherein a gas is placed within the main chamber 210 and the gas passes through the membrane.

What is claimed is:

1. A gas emitting system, the system comprising:
   a) a tube comprising a main chamber and the tube comprising a bottom end attached to a pipe plug and the tube comprising a top end attached to a neck area;
   b) the neck area defining a constricted opening, the constricted opening connected to the main chamber and the constricted opening connected to a membrane void, the membrane void defined by the neck area, the neck area comprising a flat outer surface and the neck area defining a plurality of voids perpendicular to the flat outer surface of the neck area;
   c) a top cap comprising a bottom side and top side, the top cap defining a plurality of screw voids;
   d) the top cap defining a plurality of shole voids, the shole voids surrounding a center shole void, the center shole void defined by the top cap;
   e) a permeable membrane disposed within the membrane void;
   f) a washer with the permeable membrain and a gasket in contact with the washer;
   g) the permeable membrane comprising a plurality of protrusions surrounding a center protrusion; and
   h) the plurality of protrusions of the permeable membrane enter the shole voids of the top cap and with the center protrusion of the permeable membrane enters the center shole void of the top cap.

2. The system of claim 1 wherein the permeable membrane comprises amorphous fluoropolymer.

3. The system of claim 1 wherein the permeable membrane is comprised of fluorinated (ethylenic-cyclo oxyaliphatic substituted ethylenic) copolymer.

4. The system of claim 1 wherein the permeable membrane comprises Teflon AF.

5. The system of claim 1 wherein a liquid is placed within the main chamber and the liquid passes through the membrane.

6. The system of claim 1 wherein a gas is placed within the main chamber and the gas passes through the membrane.

* * * * *